United States Patent
Murai et al.

(10) Patent No.: US 7,060,855 B2
(45) Date of Patent: Jun. 13, 2006

(54) ASYMMETRIC PHOSPHINOSELENOIC CHLORIDE AND METHOD FOR PRODUCING THE SAME

(75) Inventors: Toshiaki Murai, Gifu (JP); Tsutomu Kimura, Gifu (JP)

(73) Assignee: Gifu University, Gifu (JP)

( * ) Notice: Subject to any disclaimer, the term of this patent is extended or adjusted under 35 U.S.C. 154(b) by 0 days.

(21) Appl. No.: 10/785,517

(22) Filed: Feb. 24, 2004

(65) Prior Publication Data
US 2004/0167356 A1   Aug. 26, 2004

(30) Foreign Application Priority Data

Feb. 24, 2003   (JP)   ............................. 2003-046331
Nov. 17, 2003   (JP)   ............................. 2003-386479

(51) Int. Cl.
*C07F 9/02* (2006.01)

(52) U.S. Cl. .................................................... 562/808
(58) Field of Classification Search ................. 562/808
See application file for complete search history.

(56) References Cited

FOREIGN PATENT DOCUMENTS

JP   6-258758 A   9/1994

OTHER PUBLICATIONS

Sekar et al., Improved synthesis of HN(SPPh2)(SePPh2) and some coordination chemistry of [N(SPPh2)(SePPh2)]-, Inorganica Chimica Acta, 319 (2001), 117-122.*

Krawiecka, Reaction of thiolo- and Selenolo Esters of Phosphorus Acids with Hologens Part 5. Halogenolysis of Selenium Methyl Phoshinoselenoates, Heteroatom Chemistry (1992), 3(4), 385-394.*

Bayandina et al., Synthesis of Arylselenophosphinic Acid Derivatives and their Properties, Zhurnal Obshchei Khimi (1978), 48 (12), 2673-2677.*

Wolfsberger, Von Werner, darstellung und NMR-spektroskopische Charakterisierung einiger t-Butyl-und i-Butyl-organochlorphosphane, R(t-$C_4H_9$) PCl und R(i$C_4H_9$)PCl, Chemikler-Zeitung, vol. 110, No. 12 (1986) pp. 449-450.

* cited by examiner

*Primary Examiner*—Johann Richter
*Assistant Examiner*—Chukwuma Nwaonicha
(74) *Attorney, Agent, or Firm*—Crompton, Seager & Tufte, LLC

(57) ABSTRACT

An asymmetric phosphinoselenoic chloride of the present invention is represented by the general formula:

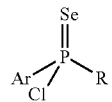

wherein Ar represents an aryl group and R represents an aryl group, an alkyl group having 3 or more carbon atoms, or an alkoxy group. The asymmetric phosphinoselenoic chloride is a novel compound and is useful as synthetic raw materials, agricultural chemicals, pharmaceutical products and the like.

8 Claims, No Drawings

ASYMMETRIC PHOSPHINOSELENOIC CHLORIDE AND METHOD FOR PRODUCING THE SAME

BACKGROUND OF THE INVENTION

The present invention relates to a novel asymmetric phosphinoselenoic chloride to be used for a variety of synthetic raw materials, agricultural chemicals, pharmaceutical products and the like and a method for producing such an asymmetric phosphinoselenoic chloride.

In a phosphinoselenoic chloride, used as a sensitizer, described in Japanese Laid-Open Patent Publication No. 6-258758, a selenium atom, a chlorine atom, an ethyl group, and a phenyl group are bonded to a phosphorus atom.

Meanwhile, it has been desired to develop a method for synthesizing a novel conjugated electron compound having a selenium atom from a phosphinoselenoic chloride. A novel conjugated electron compound having a selenium atom is expected to have a new physiological activity unlike a conventional conjugated electron compound having a selenium atom and is also expected to be useful as a basal compound.

SUMMARY OF THE INVENTION

Accordingly, it is an objective of the present invention to provide a novel asymmetric phosphinoselenoic chloride and a method for producing such an asymmetric phosphinoselenoic chloride.

To achieve the foregoing and other objectives and in accordance with the purpose of the present invention, an asymmetric phosphinoselenoic chloride is provided. The asymmetric phosphinoselenoic chloride is represented by the general formula:

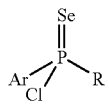

wherein Ar represents an aryl group and R represents an aryl group, an alkyl group having 3 or more carbon atoms, or an alkoxy group.

In another aspect of the present invention, a method for producing an asymmetric phosphinoselenoic chloride is provided. The method includes mixing arylphosphine dichloride, an organometallic reagent, and selenium in a solvent so as to cause a reaction of the arylphosphine dichloride, the organometallic reagent, and the selenium. The arylphosphine dichloride is represented by the general formula (1):

wherein Ar represents an aryl group. The organometallic reagent is represented by the general formula (2) or (3):

wherein R represents an aryl group, an alkyl group having 3 or more carbon atoms, or an alkoxy group; and M represents lithium or sodium,

wherein R represents an aryl group, an alkyl group having 3 or more carbon atoms, or an alkoxy group; N represents magnesium, copper, or zinc; and X represents halogen.

Other aspects and advantages of the invention will become apparent from the following description, illustrating by way of example the principles of the invention.

DETAILED DESCRIPTION OF THE PREFERRED EMBODIMENTS

One embodiment of the present invention will now be described.

An asymmetric phosphinoselenoic chloride according to the embodiment is represented by the general formula 1:

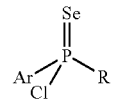

wherein Ar represents an aryl group; and R represents an aryl group, an alkyl group having 3 or more carbon atoms, or an alkoxy group.

The aryl group may include a phenyl group, a 2-methoxyphenyl group, and a 4-chlorophenyl group. The alkyl group having 3 or more carbon atoms may include an isopropyl group, a tert-butyl group, a 1-methylpropyl group, and a cycloalkyl group such as a cyclohexyl group. The alkoxy group may include a menthyloxy group.

An asymmetric phosphinoselenoic chloride represented by the formula 1, wherein Ar represents a phenyl group and R represents an isopropyl group, a cyclohexyl group, a tert-butyl group, a 2-methoxyphenyl group, a 1-methylpropyl group, a 4-chlorophenyl group, or a menthyloxy group has excellent stability in air.

Next, a method for producing the asymmetric phosphinoselenoic chloride will be described.

When the asymmetric phosphinoselenoic chloride represented by the formula 1 is produced, arylphosphine dichloride represented by the following general formula 2, an organometallic reagent represented by the following general formula 3 or 4, and selenium are added to a solvent. With this procedure, a reaction of the arylphosphine dichloride, the organometallic reagent, and the selenium is caused in the solvent according to the following reaction scheme 5 or 6 and consequently, an asymmetric phosphinoselenoic chloride are obtained together with a by-product. The ratio of the arylphosphine dichloride, the organometallic reagent, and the selenium is preferably in an equivalent ratio, (arylphosphine dichloride: organometallic reagent:selenium)=1:1:1.

   General formula 2

(wherein Ar represents an aryl group).

   General formula 3

(wherein R represents an aryl group, an alkyl group having 3 or more carbon atoms, or an alkoxy group; and M represents lithium or sodium).

   General formula 4

(wherein R represents an aryl group, an alkyl group having 3 or more carbon atoms, or an alkoxy group; N represents magnesium, copper, or zinc; and X represents halogen).

Reaction scheme 5

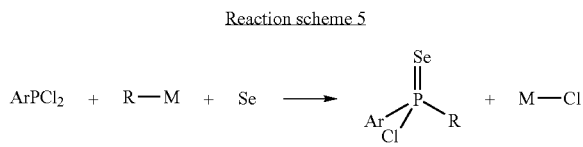

(wherein Ar represents an aryl group; R represents an aryl group, an alkyl group having 3 or more carbon atoms, or an alkoxy group; and M represents lithium or sodium).

Reaction scheme 6

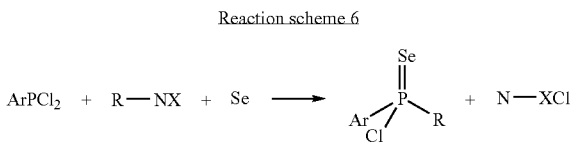

(wherein Ar represents an aryl group; R represents an aryl group, an alkyl group having 3 or more carbon atoms, or an alkoxy group; N represents magnesium, copper, or zinc; and X represents halogen).

In the reaction schemes 5 and 6, a reaction intermediate is produced first by a reaction of the arylphosphine dichloride and the organometallic reagent in the solvent and a reaction of the reaction intermediate and the selenium is caused to produce the asymmetric phosphinoselenoic chloride. Since the arylphosphine dichloride, the organometallic reagent, and the selenium have high reactivity, the reactions represented by the reaction schemes 5 and 6 proceed even when no catalyst is used.

The solvent may be any solvent generally used in synthetic organic chemistry. A preferable solvent is tetrahydrofuran (THF) and toluene since they do not inhibit the reactions and dissolve reaction products well.

The production efficiency of the asymmetric phosphinoselenoic chloride, that is, the efficiency of the reaction represented by the reaction scheme 5 or 6, depends on the reaction temperature and the reaction time. The reaction temperature is preferably 0 to 120° C. If the reaction temperature is lower than 0° C., the production efficiency may be decreased because of the slow speed of the reaction. If the reaction temperature exceeds 120° C., the solvent may be evaporated in some cases. The reaction time is preferably 30 to 90 minutes. If the reaction time is shorter than 30 minutes, the production efficiency may be decreased because the reaction insufficiently proceeds. If the reaction time exceeds 90 minutes, since side reaction is promoted, it becomes difficult to selectively obtain the asymmetric phosphinoselenoic chloride.

This embodiment has the following advantages.

According to this embodiment, a novel asymmetric phosphinoselenoic chloride is provided. The asymmetric phosphinoselenoic chloride is stable in air and has physiological activity and therefore it can be used for agricultural chemicals and pharmaceutical products. The asymmetric phosphinoselenoic chloride may also be used as a sensitizer and a synthesis raw material for various compounds. In the case where the asymmetric phosphinoselenoic chloride is used as a synthesis raw material, the asymmetric phosphinoselenoic chloride works as a supply source for a ligand such as an aryl group or as a basal compound for synthesizing a ligand.

The asymmetric phosphinoselenoic chloride represented by the formula 1, wherein Ar represents a phenyl group and R represents an isopropyl group, a cyclohexyl group, a tert-butyl group, a 2-methoxyphenyl group, a 1-methylpropyl group, a 4-chlorophenyl group, or a menthyloxy group has excellent stability in air.

Production of the asymmetric phosphinoselenoic chloride requires no catalyst. That is, the asymmetric phosphinoselenoic chloride is produced at relatively high yield merely by mixing arylphosphine dichloride, an organometallic reagent, and selenium in a solvent. Accordingly, the asymmetric phosphinoselenoic chloride is produced easily.

The asymmetric phosphinoselenoic chloride is produced at high yield and selectively when the reaction temperature is controlled to be 0 to 120° C. and the reaction time is controlled to be 30 to 90 minutes.

In the case where THF or toluene is used as the solvent, the solvent does not inhibit the reactions.

Next, examples of the present invention will be described.

EXAMPLE 1

In 40 mL of THF were dissolved 1.09 mL (8.00 mmol) of dichlorophenylphosphine and 0.695 g (8.80 mmol) of selenium to prepare a solution A. 4.00 mL (8.00 mmol; 2.0 M solution in diethyl ether) of isopropylmagnesium chloride was dissolved in 36 mL of THF to prepare a solution B. The solution B was added dropwise in 1 hour to the solution A cooled to 0° C. After the solvent was removed in vacuo from the mixed solution, the thus treated mixture was refluxed for 1 hour with 20 mL of toluene, insoluble substances were removed by filtration, and the solvent was removed again in vacuo. When the residue was purified by silica gel column chromatography (hexane dichloromethane=1:1, Rf=0.50), a colorless and oily substance stable in air was obtained. From the following result of IR absorption spectrometry, nuclear magnetic resonance spectrometry, and mass spectrometry, the substance was found to be P-1-methylethyl-P-phenylphosphinoselenoic chloride having the following structural formula 7. In Example 1, the yield rate of P-1-methylethyl-P-phenylphosphinoselenoic chloride was 91% and the yield amount was 1.927 g (7.26 mmol).

IR absorption spectrometry (KBr plate)

(neat) 3075, 3055, 2969, 2930, 2870, 1967, 1900, 1815, 1675, 1586, 1480, 1464, 1452, 1437, 1385, 1365, 1335, 1308, 1281, 1245, 1185, 1161, 1099, 1072, 1035, 1029, 998, 931, 879, 747, 710, 689, 673, 648, 617 cm$^{-1}$ NMR spectrometry (In CDCl$_3$, TMS internal standard)

$^1$H-NMR (CDCl$_3$): δ0.97 (dd, $^1J_{H-H}$=6.8 Hz, $^3J_{H-P}$=24.2 Hz, 3H, CH$_3$), 1.36 (dd, $^1J_{H-H}$=6.8 Hz, $^3J_{H-P}$=22.9 Hz, 3H, CH$_3$), 2.76 (heptet, d, 1$J_{H-H}$=6.8 Hz, $^2J_{H-P}$=9.8 Hz, 1H, CH), 7.48–7.58 (m, 3H, Ar), 7.99–8.06 (m, 2H, Ar).

$^{13}$C-NMR (CDCl$_3$): δ16.5 (d, $^2J_{C-P}$=1.7 Hz, CH$_3$), 16.7 (CH$_3$), 40.0 (d, $^1J_{C-P}$=49.6 Hz, CH), 128.6 (d, J$_{C-P}$=13.2 Hz, Ar), 131.8 (d, J$_{C-P}$=11.6 Hz, Ar), 132.0 (Ar; One half of the signal is overlapping with another signal.), 132.7 (d, $^4J_{C-P}$=3.3 Hz, Ar).

$^{31}$P-NMR (CDCl$_3$): δ100.2 ($^1J_{P-Se}$=841.9 Hz).

$^{77}$Se-NMR (CDCl$_3$): δ−219.7 (d, $^1J_{Se-P}$=841.9 Hz).

Mass spectrometry

MS (EI): m/z=266 (M$^+$).

HRMS: Calcd for C$_9$H$_{12}$ClPSe: 265.9530, Found: 265.9537.

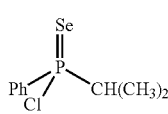

Structural formula 7

(wherein Ph represents a phenyl group).

EXAMPLE 2

In 80 mL of THF were dissolved 2.17 mL (16.0 mmol) of dichlorophenylphosphine and 1.390 g (17.6 mmol) of selenium to prepare a solution C. 8.00 mL (16.0 mmol; 2.0 M solution in diethyl ether) of cyclohexylmagnesium chloride was dissolved in 72 ml of THF to prepare a solution D. The solution D was added dropwise in 1 hour to the solution C cooled to 0° C. After the solvent was removed in vacuo from the mixed solution, the thus treated mixture was refluxed for 1 hour with 40 mL of toluene, insoluble substances were removed by filtration, and the solvent was removed again in vacuo. When the residue was purified by silica gel column chromatography (hexane: dichloromethane=1:1, Rf=0.70), a colorless and solid substance stable in air and having a melting point of 79 to 81° C. was obtained. From the following result of IR absorption spectrometry, nuclear magnetic resonance spectrometry, mass spectrometry, and elemental analysis, the substance was found to be P-cyclohexyl-P-phenylphosphinoselenoic chloride having the following structural formula 8. In Example 2, the yield rate of P-cyclohexyl-P-phenylphosphinoselenoic chloride was 96% and the yield amount was 4.680 g (15.3 mmol).

IR absorption spectrometry (KBr plate)

3075, 3051, 2944, 2936, 2925, 2875, 2854, 1977, 1959, 1914, 1897, 1822, 1809, 1771, 1684, 1669, 1615, 1585, 1574, 1480, 1449, 1437, 1385, 1344, 1335, 1309, 1295, 1269, 1200, 1185, 1173, 1161, 1123, 1112, 1097, 1078, 1046, 1026, 999, 976, 918, 886, 850, 821, 793, 754, 740, 708, 688, 617 cm$^{-1}$

NMR spectrometry (In CDCl$_3$, TMS internal standard)

$^1$H-NMR (CDCl$_3$): δ1.12–1.38 (m, 4H, CH$_2$), 1.50–1.77 (m, 4H, CH$_2$), 1.88–1.92 (m, 1H, CH), 2.13–2.17 (m, 1H, CH), 2.39–2.49 (m, 1H, CH), 7.47–7.56 (m, 3H, Ar), 7.98–8.03 (m, 2H, Ar).

$^{13}$C-NMR (CDCl$_3$): δ25.4 (d, J$_{C-P}$=1.7 Hz, CH$_2$), 25.7 (d, J$_{C-P}$=7.4 Hz, CH$_2$), 25.8 (d, J$_{C-P}$=5.6 Hz, CH$_2$), 26.0 (d, J$_{C-P}$=3.3 Hz, CH$_2$), 26.3 (CH$_2$), 49.4 (d, $^1$J$_{C-P}$=47.4 Hz, CH), 128.5 (d, J$_{C-P}$=13.2 Hz, Ar), 131.9 (d, J$_{C-P}$=11.2 Hz, Ar), 132.1 (d, $^1$J$_{C-P}$=71.1 Hz, Ar), 132.6 (d, $^4$J$_{C-P}$=3.3 Hz, Ar).

$^{31}$P-NMR (CDCl$_3$): δ95.8 ($^1$J$_{P-Se}$=840.4 Hz).

$^{77}$Se-NMR (CDCl$_3$): δ–196.5 (d, $^1$J$_{Se-P}$=840.4 Hz).

Mass spectrometry

MS (EI): m/z=306 (M$^+$).

HRMS: Calcd for C$_{12}$H$_{16}$ClPSe: 305.9843, Found: 305.9874.

Elemental analysis

Anal. Calcd for C$_{12}$H$_{16}$ClPSe(305.64): C, 47.16; H, 5.28, Found: C, 47.33; H, 5.18.

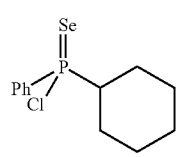

Structural formula 8

(wherein ph represents a phenyl group).

EXAMPLE 3

In 100 mL of THF were dissolved 2.71 mL (20.0 mmol) of dichlorophenylphosphine and 1.737 g (22.0 mmol) of selenium to prepare a solution E. 20.00 mL (20.0 mmol; 1.0 M solution in THF) of sec-butyl magnesium chloride was dissolved in 80 mL of THF to prepare a solution F. The solution F was added dropwise in 1 hour to the solution E cooled to 0° C. After the solvent was removed in vacuo from the mixed solution, the thus treated mixture was refluxed for 1 hour with 40 mL of toluene, insoluble substances were removed by filtration, and the solvent was removed again in vacuo. When the residue was purified by silica gel column chromatography (hexane: dichloromethane=1:1, Rf=0.60), a pale yellow and oily substance stable in air was obtained. From the following result of IR absorption spectrometry, nuclear magnetic resonance spectrometry, and mass spectrometry, the substance was found to be P-1-methylpropyl-P-phenylphosphinoselenoic chloride (diastereomer mixture) having the following structural formula 9. In Example 3, the yield rate of P-1-methylpropyl-P-phenylphosphinoselenoic chloride was 82% and the yield amount was 4.602 g (16.5 mmol).

IR absorption spectrometry (KBr plate)

3057, 2969, 2932, 2874, 2681, 1966, 1899, 1814, 1775, 1678, 1586, 1480, 1460, 1437, 1381, 1335, 1309, 1218, 1184, 1152, 1098, 1071, 1047, 1014, 998, 978, 848, 781, 746, 713, 688, 662, 642, 618 cm$^{-1}$

NMR spectrometry (In CDCl$_3$, TMS internal standard)

$^1$H-NMR (CDCl$_3$): δ0.85, 1.04 (d, J=7.8 Hz, 3H, CH$_3$ in CH$_2$CH$_3$), 0.94, 1.36 (dd, J=6.8, 24.9 Hz, 3H, CH$_3$ in CHCH$_3$), 1.22–1.58, 2.03–2.17 (m, 2H, CH$_2$), 2.44–2.56 (m, 1H, CH), 7.44–7.57 (m, 3H, Ar), 7.95–8.01 (m, 2H, Ar).

$^{31}$P-NMR (CDCl$_3$): δ98.7 ($^1$J$_{P-Se}$=841.9 Hz).

$^{77}$Se-NMR (CDCl$_3$): δ–206.9 (d, $^1$J$_{Se-P}$=841.9 Hz), –205.0 (d, $^1$J$_{Se-P}$=841.9 Hz).

Mass spectrometry

MS (EI): m/z=280 (M$^+$).

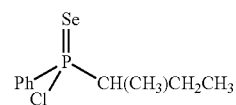

Structural formula 9

(wherein Ph represents a phenyl group).

EXAMPLE 4

In 150 mL of THF were dissolved 4.07 mL (30.0 mmol) of dichlorophenylphosphine and 2.606 g (33 mmol) of selenium to prepare a solution G. 30.00 mL (30.0 mmol; 1.0 M solution in THF) of tert-butyl magnesium chloride was dissolved in 120 mL of THF to prepare a solution H. The solution H was added dropwise in 1 hour to the solution G cooled to 0° C. After the solvent was removed in vacuo from the mixed solution, the thus treated mixture was refluxed for 1 hour with 80 mL of toluene, insoluble substances were removed by filtration, and the solvent was removed again in vacuo. When the residue was purified by silica gel column chromatography (hexane:dichloromethane=1:1, Rf=0.40), a colorless and solid substance stable in air and having a melting point of 72° C. to 74° C. was obtained. From the following result of IR absorption spectrometry, nuclear magnetic resonance spectrometry, mass spectrometry, and elemental analysis, the substance was found to be P-1,1-dimethylethyl-P-phenylphosphinoselenoic chloride having the following structural formula 10. In Example 4, the yield rate of P-1,1-dimethylethyl-P-phenylphosphinoselenoic chloride was 94% and the yield amount was 7.524 g (26.9 mmol).

IR absorption spectrometry (KBr plate)
3075, 3053, 2966, 2945, 2925, 2899, 2865, 1982, 1960, 1917, 1893, 1806, 1671, 1584, 1473, 1457, 1435, 1390, 1362, 1335, 1308, 1281, 1185, 1170, 1098, 1073, 1028, 1013, 998, 970, 937, 801, 743, 706, 688, 622, 612 cm$^{-1}$ NMR spectrometry (In CDCl$_3$, TMS internal standard)
$^1$H-NMR (CDCl$_3$): δ1.25 (d, $^3J_{H-P}$=21.0 Hz, 9H, CH$_3$), 7.45–7.56 (m, 3H, Ar), 8.00–8.06 (m, 2H, Ar).
$^{13}$C-NMR (CDCl$_3$): δ24.7 (d, $^2J_{C-P}$=2.5 Hz, CH$_3$), 42.7 (d, $^1J_{C-P}$=43.0 Hz, C binding to CH$_3$ in CCH$_3$), 128.1 (d, $J_{C-P}$=12.4 Hz, Ar), 130.7 (d, $^1J_{C-P}$=67.0 Hz, Ar), 132.4 (d, $^4J_{C-P}$=2.5 Hz, Ar), 133.1 (d, $J_{C-P}$=10.8 Hz, Ar).
$^{31}$P-NMR (CDCl$_3$): δ111.0 ($^1J_{P-Se}$=837.3 Hz).
$^{77}$Se-NMR (CDCl$_3$): δ−171.5 (d, $^1J_{Se-P}$=837.3 Hz).
Mass spectrometry
MS (EI): m/z=280 (M$^+$).
HRMS: Calcd for C$_{10}$H$_{14}$ClPSe: 279.9686, Found: 279.9682.
Elemental analysis
Anal. Calcd for C$_{10}$H$_{14}$ClPSe(279.60): C, 42.96; H, 5.05, Found: C, 42.95; H, 4.87.

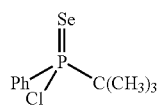

Structural formula 10

(wherein Ph represents a phenyl group).

EXAMPLE 5

In 40 mL of THF were dissolved 5.45 mL (40.0 mmol) of dichlorophenylphosphine and 3.474 g (44 mmol) of selenium to prepare a solution I. 8.00 mL (8.0 mmol; 1.0 M solution in THF) of 2-methoxyphenyl magnesium bromide was dissolved in 32 mL of THF to prepare a solution J. The solution J was added dropwise in 1 hour to the solution I cooled to 0° C. After the solvent was removed in vacuo from the mixed solution, the thus treated mixture was refluxed for 1 hour with 20 mL of toluene, insoluble substances were removed by filtration, and the solvent was removed again in vacuo. When the residue was purified by silica gel column chromatography (hexane:dichloromethane=1:1, Rf=0.40) and gel permeation chromatography (GPC), a colorless and oily substance stable in air was obtained. From the following result of IR absorption spectrometry, nuclear magnetic resonance spectrometry, and mass spectrometry, the substance was found to be P-2-methoxyphenyl-P-phenylphosphinoselenoic chloride having the following structural formula 11. In Example 5, the yield rate of P-2-methoxyphenyl-P-phenylphosphinoselenoic chloride was 38% and the yield amount was 0.497 g (1.51 mmol).

IR absorption spectrometry (KBr plate)
(neat) 3370, 3059, 3007, 2966, 2933, 2837, 1586, 1573, 1473, 1462, 1434, 1385, 1278, 1250, 1180, 1018, 800, 750, 709, 688 cm$^{-1}$ NMR spectrometry (In CDCl$_3$, TMS internal standard)
$^1$H-NMR (CDCl$_3$): δ3.59 (s, 3H, OCH$_3$), 6.87 (t, J=7.8 Hz, 1H, Ar), 7.10–7.15 (m, 1H, Ar), 7.40–7.50 (m, 3H, Ar), 7.52–7.57 (m, 1H, Ar), 7.85–7.91 (m, 2H, Ar), 8.14–8.20 (m, 1H, Ar).
$^{13}$C-NMR (CDCl$_3$): δ55.6 (OCH$_3$), 112.2 (d, $J_{C-P}$=6.6 Hz, Ar), 120.8 (d, $J_{C-P}$=15.7 Hz, Ar), 121.7 (d, $^1J_{C-P}$=82.7 Hz, Ar), 128.1 (d, $J_{C-P}$=14.9 Hz, Ar), 130.3 (d, $J_{C-P}$=13.2 Hz, Ar), 131.8 (d, $J_{C-P}$=3.3 Hz, Ar), 135.3 (d, $J_{C-P}$=12.4 Hz, Ar), 135.4 (d, $J_{C-P}$=1.7 Hz, Ar), 136.5 (d, $^1J_{C-P}$=89.3 Hz, Ar), 159.7 (d, $J_{C-P}$=2.5 Hz, Ar).
$^{31}$P-NMR (CDCl$_3$): δ66.3 ($^1J_{P-Se}$=840.4 Hz).
$^{77}$Se-NMR (CDCl$_3$): δ−48.4 (d, $^1J_{Se-P}$=840.4 Hz).
Mass spectrometry
MS (EI): m/z=330 (M$^+$)
HRMS: Calcd for C$_{13}$H$_{12}$ClOPSe: 329.9480, Found: 329.9478.

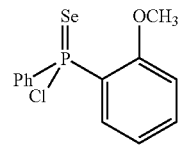

Structural formula 11

(wherein Ph represents a phenyl group).

EXAMPLE 6

The solution I was prepared in the same manner as in Example 5. 8.00 mL (8.0 mmol; 1.0 M solution in THF) of 4-chlorophenylmagnesium bromide was dissolved in 32 mL of THF to prepare a solution K. The solution K was added dropwise in 1 hour to the solution I cooled to 0° C. After the solvent was removed in vacuo from the solution mixture, the solution mixture was refluxed for 1 hour with 20 mL of toluene, insoluble substances were removed by filtration, and the solvent was removed again in vacuo. When the residue was purified by silica gel column chromatography (hexane dichloromethane=1:1, Rf=0.60), a colorless and oily substance stable in air was obtained. From the following result of IR absorption spectrometry, nuclear magnetic resonance spectrometry, and mass spectrometry, the substance was found to be P-4-chlorophenyl-P-phenylphosphinoselenoic chloride having the following structural formula 12. In Example 6, the yield rate of P-4-chlorophenyl-P-phenylphosphinoselenoic chloride was 68% and the yield amount was 1.819 g (5.45 mmol).

IR absorption spectrometry (KBr plate)
3076, 3057, 2957, 2677, 1577, 1479, 1436, 1389, 1335, 1307, 1249, 1183, 1160, 1108, 1094, 1084, 1012, 821, 744, 711, 688, 631, 618 cm$^{-1}$ NMR spectrometry (In CDCl$_3$, TMS internal standard)
$^1$H-NMR (CDCl$_3$): δ7.43–7.57 (m, 5H, Ar), 7.82–7.95 (m, 4H, Ar).

$^{13}$C-NMR (CDCl$_3$) δ128.7 (d, J$_{C-P}$=13.2 Hz, Ar), 128.9 (d, J$_{C-P}$=14.9 Hz, Ar), 131.1 (d, J$_{C-P}$=13.2 Hz, Ar), 132.5 (d, J$_{C-P}$=14.1 Hz, Ar), 132.8 (d, $^4$J$_{C-P}$=3.3 Hz, Ar), 133.9 (d, $^1$J$_{C-P}$=86.8 Hz, Ar), 134.9 (d, $^1$J$_{C-P}$=85.2 Hz, Ar), 139.3 (d, $^4$J$_{C-P}$=3.3 Hz, Ar).
$^{31}$P-NMR (CDCl$_3$): δ69.6 ($^1$J$_{P-Se}$=853.9 Hz).
$^{77}$Se-NMR (CDCl$_3$): δ−67.3 (d, $^1$J$_{Se-P}$=853.9 Hz).
Mass spectrometry
MS (EI): m/z=334 (M$^+$).

Structural formula 12

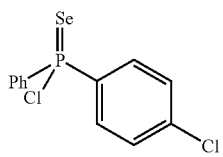

(wherein Ph represents a phenyl group).

EXAMPLE 7

In 20 mL of THF were dissolved 0.55 mL (4.0 mmol) of dichlorophenylphosphine and 0.347 g (4.4 mmol) of selenium to prepare a solution L. 0.625 g (4.0 mmol) of (−)-menthol was dissolved in 20 mL of THF and further 2.5 mL (4.0 mmol; 1.6 M solution in hexane) of butyl lithium cooled to 0° C. was added thereto and the mixture was stirred for 10 minutes to prepare a solution M. The solution M was added dropwise in 1 hour to the solution L cooled to 0° C. After the solvent was removed in vacuo from the mixed solution, the thus treated mixture was refluxed for 1 hour with 20 mL of toluene, insoluble substances were removed by filtration, and the solvent was removed again in vacuo. When the residue was purified by silica gel column chromatography (hexane:dichloromethane=1:1, Rf=0.60), a pale yellow and oily substance stable in air was obtained. From the following result of nuclear magnetic resonance spectrometry and mass spectrometry, the substance was found to be P-phenylphosphonoselenoic chloride O-(−)-menthyl ester (diastereomer mixture) having the following structural formula 13. In Example 7, the yield rate of P-phenylphosphonoselenoic chloride O-(−)-menthyl ester was 89% and the yield amount was 1.350 g (3.6 mmol).

NMR spectrometry (In CDCl$_3$, TMS internal standard)
$^1$H-NMR (CDCl$_3$): δ0.73–2.50 (m, 18H, CH3, CH2, CH), 4.71–4.88 (m, 1H, CH), 7.46–7.56 (m, 3H, Ar), 7.89–8.02 (m, 2H, Ar).
$^{31}$P-NMR (CDCl$_3$): δ82.6 ($^1$J$_{P-Se}$=908.0 Hz).
$^{77}$Se-NMR (CDCl$_3$): δ−71.1 (d, $^1$J$_{Se-P}$=908.0 Hz), −56.7 (d, $^1$J$_{Se-P}$=908.0 Hz).
Mass spectrometry
MS (EI): m/z=378 (M$^+$).

Structural formula 13

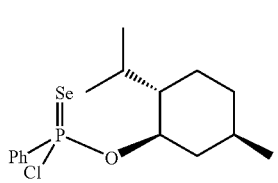

(wherein Ph represents a phenyl group).

The present examples and embodiments are to be considered as illustrative and not restrictive, and the invention is not to be limited to the details given herein, but may be modified within the scope and equivalence of the appended claims.

The invention claimed is:

1. A method for producing an asymmetric phosphinoselenoic chloride, the method comprising:
   mixing arylphosphine dichloride, an organometallic reagent, and selenium in a solvent so as to cause a reaction of the arylphosphine dichloride, the organometallic reagent, and the selenium,
   wherein the arylphosphine dichloride is represented by the general formula (1):

ArPCl$_2$ (1)

wherein Ar represents an aryl group; and
   the organometallic reagent is represented by the general formula (2) or (3):

R-M (2)

wherein R represents an aryl group, an alkyl group having 3 or more carbon atoms, or an alkoxy group; and M represents lithium or sodium,

R-NX (3)

wherein R represents an aryl group, an alkyl group having 3 or more carbon atoms, or an alkoxy group; N represents magnesium, copper, or zinc; and X represents halogen.

2. The method according to claim 1, wherein Ar in the general formula (1) represents a phenyl group and R in the general formulas (2) and (3) represents an isopropyl group, a cyclohexyl group, a tert-butyl group, a 2-methoxyphenyl group, a 1-methylpropyl group, a 4-chlorophenyl group, or a menthyloxy group.

3. The method according to claim 1, wherein the reaction of the arylphosphine dichloride, the organometallic reagent, and the selenium is carried out at a temperature of 0 to 120° C.

4. The method according to claim 1, wherein the reaction of the arylphosphine dichloride, the organometallic reagent, and the selenium is carried out for 30 to 90 minutes.

5. The method according to claim 1, wherein the reaction of the arylphosphine dichloride, the organometallic reagent, and the selenium is carried out at a temperature of 0 to 120° C. for 30 to 90 minutes.

6. The method according to claim 1, wherein the solvent is tetrahydrofuran or toluene.

7. The method according to claim 1, wherein said mixing arylphosphine dichloride, an organometallic reagent, and selenium in a solvent is carried out by mixing a solvent containing arylphosphine dichloride and selenium and a solvent containing an organometallic reagent.

8. The method according to claim 1, wherein the reaction of the arylphosphine dichloride, the organometallic reagent, and the selenium is carried out by causing a reaction of the selenium with a reaction intermediate obtained by a reaction of the arylphosphine dichloride and the organometallic reagent.

* * * * *